(12) United States Patent
Lopez Mas et al.

(10) Patent No.: US 9,132,104 B2
(45) Date of Patent: Sep. 15, 2015

(54) FORTIFICATION OF NUTRITIONAL PRODUCTS WITH OLIVE EXTRACTS CONTAINING HYDROXYTYROSOL AND HYDROXYTYROSOL FORTIFIED NUTRITIONAL PRODUCTS

(71) Applicant: PROBELTE PHARMA S.A., Espinardo (ES)

(72) Inventors: Jose A. Lopez Mas, Murcia (ES); Marcos Penalver Mellado, Murcia (ES)

(73) Assignee: PROBELTE PHARMA S.A., Espinardo (ES)

( * ) Notice: Subject to any disclaimer, the term of this patent is extended or adjusted under 35 U.S.C. 154(b) by 362 days.

(21) Appl. No.: 13/668,932

(22) Filed: Nov. 5, 2012

(65) Prior Publication Data
US 2013/0309300 A1 Nov. 21, 2013

Related U.S. Application Data

(63) Continuation of application No. 12/669,840, filed as application No. PCT/IB2008/001907 on Jul. 23, 2008, now abandoned.

(30) Foreign Application Priority Data

Jul. 23, 2007 (EP) .................................. 07014390

(51) Int. Cl.
| | |
|---|---|
| A61K 36/00 | (2006.01) |
| A61K 31/05 | (2006.01) |
| A23D 7/005 | (2006.01) |
| A23D 9/007 | (2006.01) |
| A23L 1/30 | (2006.01) |
| A61K 36/63 | (2006.01) |
| C11B 5/00 | (2006.01) |

(52) U.S. Cl.
CPC ............. *A61K 31/05* (2013.01); *A23D 7/005* (2013.01); *A23D 7/0056* (2013.01); *A23D 9/007* (2013.01); *A23L 1/3002* (2013.01); *A61K 36/63* (2013.01); *C11B 5/0035* (2013.01); *C11B 5/0085* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,998,641 A | 12/1999 | Ganguli et al. | |
| 6,162,480 A | 12/2000 | Van Buuren et al. | |
| 6,187,356 B1 * | 2/2001 | van Buuren et al. | 426/417 |
| 6,942,890 B1 | 9/2005 | Van Buuren et al. | |
| 2002/0058078 A1 | 5/2002 | Crea | |
| 2006/0003947 A1 * | 1/2006 | Udell | 514/26 |
| 2006/0070953 A1 | 4/2006 | Villanova et al. | |
| 2010/0184868 A1 | 7/2010 | Lopez Mas et al. | |

FOREIGN PATENT DOCUMENTS

| | | |
|---|---|---|
| EP | 1 582 512 | 10/2005 |
| WO | WO 2007/013032 A | 2/2007 |
| WO | WO 2007/074490 A | 7/2007 |
| WO | WO 2008/090460 A | 7/2008 |

OTHER PUBLICATIONS

Fernandez-Bolanos et al, Production in large quantities of highly purified hydroxytyrosol from liquid-solid waste of two-phase olive oil processing or "Alperujo", Journal of agricultural and food chemistry, (Nov. 6, 2002) vol. 50, No. 23, pp. 6804-6811.*

Fernandez-Bolanos et al, Production in large quantities of highly purified hydroxytyrosol from liquid-solid waste of two-phase olive oil processing or "Alperujo", Journal of Agricultural and Food Chemistry, (Nov. 6, 2002), vol. 50, No. 23, pp. 6804-6811.

* cited by examiner

*Primary Examiner* — Qiuwen Mi
(74) *Attorney, Agent, or Firm* — RatnerPrestia

(57) ABSTRACT

The present invention relates to nutritional products containing hydroxytyrosol, particularly fond products (i.e.: fortified edible oils and fortified edible oil-containing products) and dietary supplements (i.e.: soft gel capsules containing fortified edible oils) with increased antioxidant capacity to be used as a source of hydroxytyrosol for preventing or treating cardiovascular diseases, plaque build-up in the arteries, arterial hypertension, and metabolic syndrome, thanks to the nutritional supply of an hydroxytyrosol rich composition.

17 Claims, 7 Drawing Sheets

** indicates differences with control group 1 assessed by the Tukey test and P <0.001

*: indicates differences with control group 1 assessed by the Tukey test and P<0.05
** indicates differences with control group 1 assessed by the Tukey test and P <0.001

** indicates differences with control group 1 assessed by the Tukey test and P <0.001

*: indicates differences with control group 1 assessed by the Tukey test and P<0.05
** indicates differences with control group 1 assessed by the Tukey test and P <0.001

FORTIFICATION OF NUTRITIONAL PRODUCTS WITH OLIVE EXTRACTS CONTAINING HYDROXYTYROSOL AND HYDROXYTYROSOL FORTIFIED NUTRITIONAL PRODUCTS

The present application is a continuation of application Ser. No. 12/669,840, filed Mar. 19, 2010 (pending and published as US 2010-0184868 A1 on Jul. 22, 2010), which is a 371 US national phase of International Application No. PCT/IB08/01907, filed Jul. 23, 2008 (and published as WO 2009/013596 A2 on Jan. 29, 2009), which claims benefit of EP 07014390.4, filed Jul. 23, 2007, the entire contents of each of which being incorporated herein by reference.

FIELD OF THE INVENTION

The present invention relates to fortification of nutritional products with olive extracts containing hydroxytyrosol; it also relates to hydroxytyrosol fortified nutritional products and to the use of both olive extracts and the nutritional products fortified with olive extracts for medical use, in particular for prevention or treatment of cardiovascular diseases (CVD), plaque build-up in the arteries, arterial hypertension, and metabolic syndrome.

According to the invention, olive extract derived from olive fruit or olive oil extraction residues (pomace) is added to an edible oil and through this oil, to nutritional products, which results in an increase of the level of hydroxytyrosol. More particularly, the invention relates to the fortification of edible oil-containing products to be used as a source of hydroxytyrosol for preventing or treating cardiovascular diseases, plaque build-up in the arteries, arterial hypertension, and metabolic syndrome, thanks to the nutritional supply of a hydroxytyrosol rich and purified composition.

BACKGROUND OF THE INVENTION

According to the supplement published by the British Heart Foundation: European cardiovascular disease statistics, 2005 edition, CVD are the main cause of death in Europe: accounting for over 4.35 million deaths each year. Coronary heart disease (CHD) by itself is the single most common cause of death in Europe: accounting for 1.95 million deaths in Europe each year.

This supplement included a new section on economic costs estimation of CVD. Total costs of CVD is amount to 169 billion euros, of which 105 billion euros are for treating CVD in the European Union and 64 billion euros are due to lost productivity and the cost of informal care.

Plaque builds up in the arteries, also called atherosclerosis is the main cause of CVD and the most frequent cause of CHD. Atherosclerotic plaque builds up in the arteries is a common disorder of the arteries. It occurs when fat, cholesterol, and other substances build up in the walls of arteries and form hard substances called plaque.

Eventually, the plaque deposits can make the artery narrow and less flexible. This makes it harder for blood to flow. If the coronary arteries become narrow, blood flow to the heart can slow down or stop, causing chest pain (stable angina), shortness of breath, heart attack, and other symptoms.

Pieces of plaque can break apart and move through the bloodstream. This is a common cause of heart attack and stroke. Blood clots can also form around the plaque deposits. Clots block blood flow. If the clot moves into the heart, lungs, or brain, it can cause a stroke, heart attack, or pulmonary embolism.

It has been demonstrated that arterial hypertension, high levels of triglycerides and total cholesterol in the blood, and smoking are factors that contribute to the development of this affection. In recent years, researchers have found that some of these risk factors cluster together in certain people. This clustering of risk factors is known as metabolic syndrome.

People with metabolic syndrome have a clustering of the following risk factors:

Central obesity, meaning extra weight in the abdominal (stomach) area.

Trouble digesting a type of sugar called glucose (glucose intolerance). Patients with metabolic syndrome usually have hyperinsulinemia or type 2 diabetes.

High levels of low-density lipoprotein (LDL) and triglycerides in the bloodstream.

Low levels of high-density lipoprotein (HDL) in the bloodstream.

High blood pressure (hypertension).

There is still a lot to be learned about metabolic syndrome, but doctors do know that people with metabolic syndrome have an increased risk of CVD.

Numerous studies have demonstrated that in vivo oxidation of LDL plays a central role in the development of atherosclerosis (Knight, 1995; Witzum, 1994).

Olive oil, the principal fat component of the Mediterranean diet, has been associated with a lower incidence of CHD (De Lorgeril et al., 1999; Hertog et al., 1993; Mattson and Grundy, 1985) and certain cancers (d'Amicis and Farchi, 1999; Braga et al., 1998; Trichopoulou et al., 1995; Martin-Moreno et al., 1994).

Health benefits of olive oil consumption in preventing LDL oxidation would be linked both to its antioxidant and to its high monounsaturated fatty acids content (Nicolaïew et al., 1998). Virgin olive oil phenolic compounds have strong antioxidant properties that protect olive oil from oxidation (Visioli et al., 1998; Papadopoulos and Boskou, 1991), and in addition they have shown positive health benefits (Owen et al., 2000; Manna et al., 1999). Some of the most representative phenolic compounds in virgin olive oil are hydroxytyrosol, tyrosol and some of their derivatives, which are extracted from the olive fruit during olive oil production (Brenes et al., 1999). Hydroxytyrosol is present in olive oil and has the following formula:

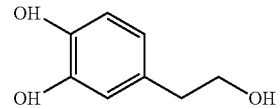

In co-pending patent applications EP07001791 and PCT/IB2008/000173, process and apparatus for the production of hydroxytyrosol from olives and/or olive oil extraction residues are described, which aim at the production of hydroxytyrosol-containing products or extracts to be used as a source of hydroxytyrosol in food, medical and cosmetic industries. The content of the above applications is hereto incorporated by reference.

It is well known that several sensory properties are elicited by olive polyphenols in extra virgin and virgin olive oils. The sensory aspect of these olive oils has great repercussions on its acceptability by consumers. Some phenols mainly elicit the tasting perception of bitterness; however, other phenolic molecules can stimulate the free endings of the trigeminal nerve located in the palate and also in the gustative buds giving rise to the chemesthetic perceptions of pungency, astringency and metallic attributes.

Oleuropein, the phenolic compound that makes the fruit of the olive bitter, is water-soluble rather than fat-soluble, so it get poorly transferred into the oil when the fruit is pressed, thus ranging average content of oleuropein from 1 ppb to 11 ppm in extra virgin and virgin olive oils.

Oleuropein is present in olive oil and has the following formula:

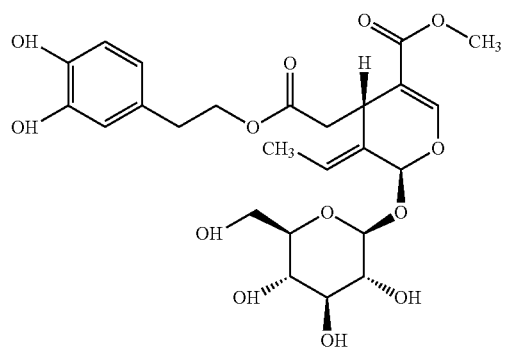 [SMILES: C/C=C1/[C@H](O[C@@H]2O[C@H](CO)[C@@H](O)[C@H](O)[C@H]2O)OC=C(C(=O)OC)[C@H]1CC(=O)OCCc1ccc(O)c(O)c1]

Nevertheless, a number of oleuropein related compounds are more oil soluble than oleuropein itself, and do end up at a higher content in the oil, in the form of isomer (or isomers) of oleuropein aglycon (e.g: aldehydic form of oleuropein aglycon, AOA), and dialdehydic form of elenolic acid linked to hydroxytyrosol or tyrosol, respectively named 3,4-DHPEA-EDA and p-HPEA-EDA, that are the olive polyphenols mainly responsible for the bitter taste according to Gutierrez-Rosales and co-authors, J. Agric. Food Chem. 2003, 51, 6021-6025.

Oleuropein aglycon (e.g: aldehydic form of oleuropein aglycon) is present in olive oil and has the following formula:

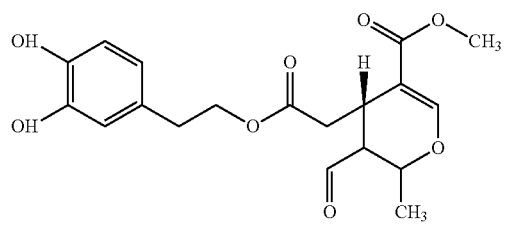 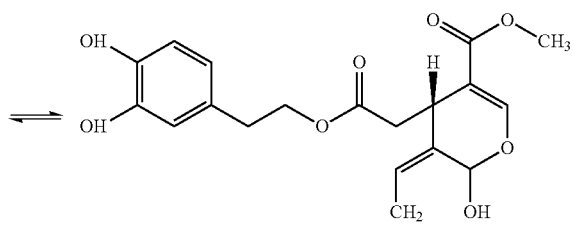

ALDEHYDIC FORM OF OLEUROPEIN AGLYCON

Frank and co-authors in *J. Agric. Food Chem.* 2001, 49, 231-238 disclose a procedure called "taste dilution analysis" in order to point out the sensory threshold of bitter for oleuropein derivatives. Bitterness was assessed by preparing serial dilutions of samples in water and then tasting them according to increasing concentration, until the concentration at which the diluted sample can be differentiated from water as judged in a triangle test is found. It was also shown that at least for these compounds there is no direct correlation of bitterness with the absorbance at 225 (the K225 value): Mateo et al. *J. Am. Oil Chem. Soc.* 2004, 81, 71-75, verified the correlation between the aldehydic form of oleuropein aglycon (obtained by hydrolysis of oleuropein with β-glucosidase from almonds purchased from Sigma) and bitterness.

Andrewes et al., J. Agric. Food Chem. 2003, 51, 1415-1420, assessed the relationship between polyphenols and olive oil pungency; p-HPEA-EDA was the key source of the burning sensation found in many olive oils.

In 2005, Beauchamp and co-authors, Nature 2005, 437, 45-46, measured the pungent intensity of p-HPEA-EDA isolated from different extra virgin and virgin olive oils confirming this molecule is the principal agent in extra virgin and virgin olive oils responsible for throat irritation.

Summarizing, any way set up in order to increase antioxidant capacity using techniques based on fortification of olive oil with olive polyphenols, should not alter oils natural organoleptic characteristics, nor increase the amount of the bitter tasting olive polyphenols, otherwise incurring with the subsequent alteration of organoleptic properties of the oil, thus causing non-pleasant taste due to excessive bitterness, pungency and/or astringency, and subsequently causing rejection from many consumers.

It is known to add polyphenols and hydroxytyrosol to food products.

U.S. Pat. No. 6,942,890 discloses a method of fortifying food products adding to such products solid matter derived from olive fruits, resulting in an increase of the level of antioxidants, particularly of olive polyphenols. This process requires the incubation during a certain time of the food product to be fortified, e.g. a vegetable oil, with solid matter derived from olives which have not been subjected to a debittering treatment, and then separating the solid from the oil by filtration. The main problem connected with this process is associated with alteration of organoleptic properties of the vegetable oil, causing non-pleasant taste when excessive bitterness and/or astringency are produced in relation when oil increases its contents of polyphenols. According to the inventors, this alteration could be avoided particularly when the final product obtained is produced adding as much a 2.5% of olive solid matter that makes extra virgin olive oils increase olive polyphenols from 145 ppm to 530 ppm as maximum.

U.S. Pat. No. 6,162,480 discloses a method of fortifying vegetable oil with antioxidants. Non-debittered olives are soaked from 1 to 30 days in vegetable oil, resulting in an increase of the level of antioxidants, particularly of olive polyphenols. According ex. 1, adding 10% non-debittered olives from Toscane were slowly stirred for 30 days with Toscane extra virgin olive oil, that makes extra virgin olive oils increase olive polyphenols from 420 ppm to 591 ppm, being this the maximum increase allowed according the invention. This method is substantially the same as the well known one used to preserve olives in olive oil, apart from the stirring.

The main problem connected with methods disclosed in U.S. Pat. No. 6,942,890 and U.S. Pat. No. 6,162,480 is that only polyphenols that are fat soluble are (partly) extracted from olive solid matter or olives into oil.

U.S. Pat. No. 6,746,706 discloses a method of fortifying food compositions (spreads, vinaigrette and tomato sauce), where such compositions containing 20-100 wt % of an aqueous phase characterized by an enhanced content of tyrosol and hydroxytyrosol in aqueous phase being at least 15 ppm. Nevertheless, this method is scarcely effective: none of the patent examples shows that the prepared food compositions reach concentrations in the water phase higher than 50 ppm for hydroxytyrosol and tyrosol together.

U.S. Pat. No. 6,361,803 discloses (ex. 13) a method characterized by using an olive extract produced according ex. 4 to allow an enhancement of antioxidant activity in an oil. Nevertheless, the antioxidant capacity of the control sample, 0.18 mM Trolox equivalent per gram, was only enhanced approximately three times by the method of the invention, 0.53 mM Trolox equivalent per gram.

U.S. Pat. No. 6,361,803 requires the use of organic solvents, particularly polar solvents, in order to produce an olive extract containing hydroxytyrosol with an acceptable purity grade. Polar aqueous solvents are selected among methanol, ethanol, acetonitrile or acetone, while polar organic solvents are selected, for example, among esters, amides, dimethyl sulfoxide, dioxane, DMF and their mixtures. The use of organic solvents, for example methanol that is a toxic solvent, is inconvenient, particularly when the final product obtained is to be used in the alimentary field.

The main problem connected with this process, in addition to the problem arising from the use of organic (and in some cases toxic) solvents, is that re-dissolution of olive extract rich in hydroxytyrosol disclosed on ex. 13 (antioxidant composition) needs water/ethanol/acetic acid mixture to previously dissolve the extract and give a stable emulsion in the oil to be fortified, being this procedure inconvenient in alimentary field.

IT 01326553 discloses a fortified olive oil obtained by addition of extracts deriving from olive leaves or vegetation water to olive oil. The extracts are rich in all types of polyphenols, i.e. they have a low purity of hydroxytyrosol. In fact extracts from leaves contain almost no hydroxytyrosol. The problem of this patent and of the previously disclosed patents mainly resides in the low amount of free hydroxytyrosol with respect to the total amount of polyphenols: the lower the amount of hydroxytyrosol with respect to other polyphenols, the higher is the bitterness (i.e. the bitter taste) of the fortified product for the same amount of free hydroxytyrosol in the oil.

U.S. Pat. No. 5,998,641 relates to a process of increasing the general content of polyphenols in olive oil without increasing the bitter taste. To this purpose, olive oil is emulsified with a water solution containing polyphenols and a debittering enzyme (e.g beta-glucosidase from almonds purchased from Sigma (ex.1)). Water is then removed by evaporation or ultrafiltration to avoid loss of those resulting polyphenols that are soluble in water and insoluble in oil. The problem of this method is that it is very long (at least 24 hours according to the examples and up to 100 hours) and that all the products of the enzymatic reaction, including oleuropein aglycon and sugars, remain in the oil.

It should be remarked that hydrolysis of oleuropein by β-glucosidase (e.g from almonds, purchased from Sigma), has been normally used by several authors for the preparation of an isomer (or isomers) of oleuropein aglycon that was found to be bitter with a threshold of 50 μmol (Frank and co-authors J. Agric. Food Chem. 2001, 49, 231-238). Also, Mateo et al. *J. Am. Oil Chem. Soc.* 2004, 81, 71-75, verified the correlation between the aldehydic form of oleuropein aglycon (obtained by hydrolysis of oleuropein with β-glucosidase from almonds purchased from Sigma) and bitterness. In other words, in U.S. Pat. No. 5,998,641 the result of the enzyme hydrolysis is a plurality of by-products including polyphenolic compounds that upon tasting give a bitter taste to the oil but that are not detectable with the K225 test.

Also it should be considered that water removal by evaporation has a negative influence on the sensory attributes (qualitative characteristics) of virgin olive oils because most of the volatile substances responsible of the unique aroma of this oil will be extracted together with the water during the evaporation process.

Summarizing, the above mentioned techniques are either too long or too complex, or too harsh for alimentary field, or all of the above; in addition the amount of hydroxytyrosol that can be incorporated in the edible oil without having too much bitter taste, pungent intensity or sugar and by-products content, and without losing aromatic volatile compounds, is too low to effectively protect LDL against oxidative modification to any important extent. It has also to be noted that all the above mentioned techniques allow to obtain an olive oil with an increased content of total olive polyphenols but with a low content in hydroxytyrosol with respect to the total olive polyphenols content, as present in the oil, due to the fact that most of the polyphenols incorporated to the oil are secoiridoids, oleuropein related compounds characterized by a higher oil solubility than hydroxytyrosol, that are consequently incorporated to the oil, as oleuropein aglycon (AOA), 3,4-DHPEA-EDA and p-HPEA-EDA, at a higher content than hydroxytyrosol, and that are those olive polyphenols mainly responsible for the bitter taste and pungency. The incorporation of these secoiridoids, able to produce undesirable changes in the organoleptic properties of the olive oil, is in fact directly related with the source of olive polyphenols used in all the above mentioned techniques, which in fact present a low content in hydroxytyrosol and/or a low purity degree.

SUMMARY OF THE INVENTION

It is an aim of the present invention to solve the above mentioned problems and to provide fortified edible oil and/or oil-containing food products to be used as a source of hydroxytyrosol for preventing or treating cardiovascular diseases, plaque build-up in the arteries, arterial hypertension, and metabolic syndrome, but avoiding non-pleasant alterations of organoleptic properties of the fortified foods.

It is another aim of the present invention to provide fortified edible oil and/or oil-containing food products characterized by a high amount of hydroxytyrosol, to be used as a source of hydroxytyrosol for preventing or treating cardiovascular diseases, plaque build-up in the arteries, arterial hypertension, and metabolic syndrome.

Another aim of the present invention is to provide fortified edible oil and/or oil-containing food products that, even though characterized by a high of content of hydroxytyrosol, are in the form of a stable and durable emulsion.

Again, an aim of the present invention is to provide fortified edible oil and/or oil-containing food products characterized by a high amount of very pure hydroxytyrosol. Such aims are achieved by means of the present invention that provides fortified edible oil and/or oil-containing products with olive extracts.

The process of production of such solvent-free natural olive extracts, obtained from olive fruits as well as from olive oil extraction by-products, permits to increase, in an extent never described until now, antioxidant capacity, in the fortified oil and/or oil-containing products, avoiding non-pleasant alterations of organoleptic properties of the fortified foods. An aspect of the invention relates to a process for preparing an olive extract rich in the antioxidant hydroxytyrosol.

Another aspect of the invention relates to a process for preparing the fortified oil and/or oil-containing products with olive extract, which comprises the following steps:
 a) Selecting appropriated olive extract, between liquid form and powder form, prepared from olive fruits or residues from the extraction of olive oil or pomaces, i.e the above defined residues from olive oil extractions, and rich in hydroxytyrosol. This selection depends on the nutritional product to be fortified, preferring olive extract in liquid form for fortification of edible oils, and olive extract in solid form for fortification of oil-containing products comprising at least a 10% of water.
 b) Incorporating and mixing the olive extract selected in a) with the oil and/or oil-containing products.

DESCRIPTION OF PREFERRED EMBODIMENTS

As mentioned an aspect of the invention relates to a nutritional product, comprising at least 30 ppm of hydroxytyrosol, preferably from 30 ppm to 30000 ppm of hydroxytyrosol. A preferred range, when the nutritional product is, for example, in the form of a fortified edible oil, as an homogenized emulsion, preferably a microemulsion, as well as when the nutritional product is a food product containing such a fortified edible oil, is 30 to 300 ppm, where the hydroxytyrosol content is preferably within the range of 45 ppm and 70 ppm and more preferably between 50 ppm and 60 ppm. When the nutritional product is, for example in the form of a dietary supplement consisting in an encapsulated fortified edible oil, as soft gel capsules containing an homogenized emulsion, preferably a microemulsion, the hydroxytyrosol content is within the range of 300 to 30000 ppm, preferably 500 to 3000 ppm.

The K225 value of a fortified oil according to the invention (see following explanation for examples 13 and 14) is 0.28 or less and preferably is 0.25 or less. In addition the content of AOA of said fortified oil is less than 120 ppm, preferably less than 85 ppm and more preferably less than 55.

The nutritional product according to the present invention and comprising the mentioned added olive extract, shows improved antioxidant capacity.

Finally, a fourth aspect of the invention relates to the use of the nutritional products, fortified oil and/or oil-containing products, in the prevention or treatment of cardiovascular diseases, plaque build-up in the arteries, arterial hypertension, and metabolic syndrome. As mentioned above, the first aspect of the invention relates to the preparation of an olive extract rich in the antioxidant hydroxytyrosol in a very pure form. The problem met was to enhance the incorporation of the hydrophilic hydroxytyrosol in oil; this problem was solved by means of the present invention that makes use of a process of extraction of hydroxytyrosol in absence of solvents and able to provide a final olive extract, rich in hydroxytyrosol and characterized by a very high purity degree, with respect of by-products, sugars and salts.

In one embodiment, residues of the extraction of olive oil or pomaces, could be used as starting material for hydroxytyrosol extraction. This process is described in co-pending patent applications EP-A-07001791 filed 26 Jan., 2007 and PCT/IB2008/000173 filed on 28 Jan., 2008 in the name of the present applicant, and is hereto incorporated by reference. In another embodiment, olive fruits are used as starting material for the production of olive extract, preferably green olives and more preferably whole green olives are used.

In the process following the teaching of the above mentioned applications, the extraction residues or whole olive fruits or crushed olive fruits are homogenized/mixed with demineralised water. Once the whole olive fruits or the homogeneous olive pulp mass, or residue mass, mixed with water is prepared, next step is the acidic hydrolysis in water of this mixture, carried out at a temperature comprised within 20° C. and 140° C., preferably within 70° C. and 140° C. and more preferably in a continuous sterilization system at a temperature within 110° C. to 140° C. The pH of the acidified mixture that undergoes the hydrolysis is within the range of 1.0 to 6.0. The mixture after the hydrolysis is clarified by physical methods known in the art, e.g. by filtering and/or centrifuging, to remove the whole olive fruits or the suspended solids from the hydrolysed product, and to obtain a clarified solution substantially free of solids in suspension.

According to a preferred embodiment of the invention the above steps are followed by the steps of loading the product thus obtained in at least one chromatographic column of a resin selected from acid activated anion exchange resins, and adsorbent non-ionic resins and of eluting the products retained in said chromatographic columns with water.

According to a further aspect of the invention the liquid product is concentrated e.g. by reverse osmosis concentration. According to a further step, after chromatographic purification and reverse osmosis concentration, the resulting liquid product is brought in another embodiment to a solid form, by spray drying, with carriers such as maltodextrines.

The olive extract thus obtained is very rich in hydroxytyrosol and has a low content of starting products as well as of by-products, and in general, has a very low content in sugars and in salts.

The extracts obtainable according to the above mentioned process may be either in liquid or solid form and are characterized by having a hydroxytyrosol content of at least 0.5% (w/w) and a purity of at least 40%, and preferably a content of at least 10% and a purity of at least 80% and more preferably a content of at least 35% and a purity of at least 90% (as determined by HPLC peak area measured at 280 nm). According to a preferred aspect of the invention, the hydroxytyrosol containing liquid product (olive extract in the liquid form) obtainable according to the invention, has a hydroxytyrosol content of at least 35% (w/w) or even more preferably of at least 45% (w/w), a purity of at least 90% (by HPLC 280 nm) and a total phenols content of at least 35%. According to a more preferred aspect of the invention, the hydroxytyrosol containing solid product (olive extract in the solid form) obtainable according to the invention, has a hydroxytyrosol content of at least 20% (w/w), a purity of at least 90% (by HPLC 280 nm) and a total phenols content of at least 20%.

According to a preferred aspect of the invention, the hydroxytyrosol containing solid product has a hydroxytyrosol content of at least 40% (w/w), and a purity of at least 90% (by HPLC 280 nm)

These extracts are free from organic solvents and also substantially free from sugars and salts.

The green olive extracts of the invention are preferred to the extracts of residues of olive oil production in view of their greater amount of hydroxytyrosol and of the reduced content of hydroxymethylfurfural. These extracts can be employed in cardiovascular diseases, plaque build-up in the arteries, arterial hypertension, and metabolic syndrome prevention or treatment. Also they could be employed in the preparation of dietary supplement.

A second aspect of the invention relates to a process for preparing the fortified oil and/or oil-containing products with olive extract, i.e. for preparing so-called functional food.

First step consists in the selection of the appropriated olive extract. For the fortification of oil, normally an olive extract in liquid form is selected. Such olive extract has a hydroxytyrosol content of at least 35% (w/w) or even more preferably of at least 45% (w/w) and a purity of at least 90% (by HPLC 280 nm) and a total phenol content of at least 35%. The use of such olive extracts is preferred for the fortification of oils due to the fact that a stable emulsion of the olive extract could be prepared without significant increase of the residual water present in the oil due to the little amount of olive extract needed to reach the desired antioxidant capacity in the fortified oil.

In fact, the olive extract according to the present invention, having a high content of hydroxytyrosol, a low content of undesired by-products (e.g. AOA, 3,4-DHPEA-EDA and p-HPEA-EDA) and being substantially free from sugars and salts, gives stable emulsions when incorporated into the oil to be fortified. In fact, as it is characterized by an high content of hydroxytyrosol, for example not less than 35% (w/w), small amounts of the olive extract are suitable for obtaining a fortified oil characterized by an high content of hydroxytyrosol. In addition, because of the purity of the olive extract according to the invention, which results substantially free from salts and sugars, when it is incorporated into the oil to be fortified, stable emulsions are obtained even in the absence of emulsifiers or other additives, with an immediate advantage, as the resulting fortified oil can be used in food, medical and cosmetic field.

The resulting fortified oils therefore contain at least 30 ppm of hydroxytyrosol, and retain organoleptic properties that are no adversely affected.

For fortification of oil-containing products comprising at least a 10% of water, normally an olive extract in powder form is selected. Such olive extract has a hydroxytyrosol content of at least 20% (w/w). Suitable carriers are e.g. maltodextrines, lactose, caseinates, and etcetera. The use of such olive extracts is preferred for the fortification of oil-containing products comprising at least a 10% of water, due to the fact that such powder is easily handled and completely dissolved in such nutritional products in the range employed to reach the desired antioxidant capacity in the oil-containing products.

Second step consists in incorporating the olive extract selected with the oil and/or oil-containing products. The incorporation of the olive extract to the nutritional product is obtained by mixture and homogenisation according to the technological process of each product.

Fortification of oil consists in incorporating the olive extract during its technological preparation. In general, olive extract in liquid form is added in the weight ratio desired to the oil and completely mixed, under controlled parameters of temperature and agitation; then it is necessary to let the product settle to remove the water-based olive extract in excess. To do this, it is possible to use any known method such as, for example, conventional decantation. In fact, during the production of vegetable oils, several consecutive conventional decantation steps are normal to eliminate residual water, and in a natural way the olive antioxidant could be incorporated to the oil just before the last decantation step normally done during its production. Because of the high concentration of hydroxytyrosol in the water based extract as well as because of its high purity degree, it is possible to transfer with each mixing step a good amount of hydroxytyrosol to the oil product. The water phase decanted from the oil phase usually contains some hydroxytyrosol and is therefore recovered for further use.

In a preferred embodiment of the invention, an olive extract in liquid form is added to the oil, premixed under inert atmosphere (i.e. nitrogen atmosphere) according to controlled parameters of temperature and agitation. The product is feed into a homogenizer operating according to a double stage homogenization procedure, the first stage being carried out at a pressure value comprised between 200 and 700 bar and the second stage being carried out maintaining the pressure between 30 and 50 bar. The homogenization of the pre-emulsion allows to obtain a stable emulsion.

In one embodiment of the invention, pure hydroxytyrosol is added to water and the resulting solution is mixed and homogenised with oil to transfer hydroxytyrosol to the oil phase. Preferably natural extracts according to the invention are used, so as to avoid any trace of organic solvents in the final product, especially in view of their use in the prevention and treatment of cardiovascular diseases, plaque build-up in the arteries, arterial hypertension, and metabolic syndrome.

Fortification of solid oil-containing products consists in incorporating and mixing the olive extract during its technological preparation. In general the process for the preparation of the oil containing product is characterized in that it contains: a) the presence of an oil phase, which comprises edible oil and/or edible fat and optionally further lipophilic constituents b) an emulsification step, which comprises the addition to a) of an emulsifier under controlled agitation and temperature ranges c) the presence of an aqueous phase, which contains water and, optionally further hydrophilic constituents; the weight ratio of the oil phase to the aqueous phase being in the range from 9:1 to 1:9.

Olive extract powder is added in the weight ratio desired to the water phase (c) and completely dissolved, under very controlled parameters of temperature and agitation, straight afterwards the oil phase (a), to which emulsifier was previously incorporated is added to the water phase (c) in order to create a stable o/w matrix.

A third aspect of the invention relates to a nutritional product, to which hydroxytyrosol, preferably in the form of the olive extract defined above, has been incorporated producing fortified oil and/or oil-containing products. In the context of the present invention, by the expression "nutritional product" it is meant any food product, edible product, or dietary supplement that is an edible oil or that contains at least an edible oil. The nutritional products of the invention preferably comprise a concentration of the olive extract of the invention ranging from 0.01% to 93% (w/w). A more preferred range comprise from 0.01% to 30% (w/w) of the olive extract of the invention. Nutritional products that are edible oils containing this amount of added olive extract can be for example:

a) vegetable oils obtained from various sources such us olive (extra virgin olive oil (evoo), virgin olive oil, olive oil, lampante olive oil, refined olive oil, crude olive-pomace oil, refined olive-pomace oil), sunflower, corn, soya, flax seed, almond, canola, safflower, palm, coconut, rapeseed, to name a few, technologically modified derivatives of the above mentioned oils or mixtures of two or more of the same could be used for its fortification.

b) marine or fish oils obtained from various sources such us algae, krill, menhaden, anchovy, tuna, herring, sardines, mackerel, cod to name a few, technologically modified derivatives of the above mentioned oils or mixtures of two or more of the same could be used for its fortification.

Another more preferred range comprises from 0.05% to 35% (w/w) of the olive extract of the invention. Nutritional products, that contain at least an edible oil, containing the above amount of added olive extract can be, for example: oil-containing products such as margarine, mayonnaise, garlic mayonnaise, gazpacho soup, spreadable sauces, salad dressings, to name a few, technologically modified derivatives of the above mentioned oil-containing products or mixtures of two or more of the same could be used for its fortification.

Finally a fourth aspect of the invention relates to the use of the nutritional products of the invention, fortified oil and/or oil-containing products, in the prevention or treatment of cardiovascular diseases, plaque build-up in the arteries, arterial hypertension, and metabolic syndrome.

In a preferred embodiment of the invention, an emulsion of olive extract (in liquid form) and edible oil was used to prepare soft gel capsules.

Several aspects should be considered when softgel capsules are manufactured. One aspect is related to capsule size. The upper size limit which most consumers find acceptable is about 1.2 g, that represents a size commonly used for other oil dietary supplements. The second aspect is represented by the number of capsules needed to be taken per day. Generally, the upper limit is 4 to 6 capsules per day. When the larger capsule size is considered, an oblong shape (1000 mg or more) is preferred as it is easier to swallow. The present invention is not limited by these parameters. Another consideration is the minimum dose needed for efficacy. The preferred minimum dosage for prevention or treatment of cardiovascular diseases, plaque build-up in the arteries, arterial hypertension, and metabolic syndrome is 2 g of fortified edible oil, delivering from 3 to 50 mg of hydroxytyrosol per day, which can be administered, for example, in two doses of 1 g of fortified edible oil per day.

BRIEF DESCRIPTION OF THE DRAWINGS

The invention will now be further disclosed in greater detail with reference to the enclosed following non-limiting examples and drawings wherein:

FIG. 11 is related to example 12, where the animal groups were organized according to Table 6. The invention will now be further discussed with reference to the following non-limiting examples.

EXAMPLE 1

Olive Extracts Production from Olives Fruits

Figure 1:
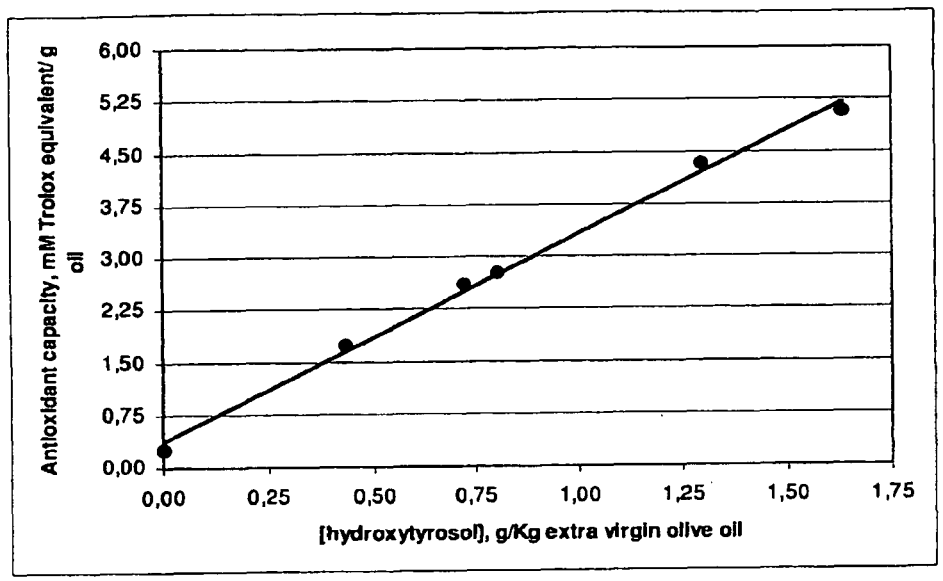
FIGS. 1-5 are graphs showing the linear correlation between the antioxidant capacity of different nutritional products obtained according the present invention (see examples 3 to 7) and their content in hydroxytyrosol measured by HPLC as a result of their fortification with increasing quantities of olives extracts obtained according to the present invention.

25 Kg of a sample of olives fruits are mixed with 50 L of demineralised water. The obtained mixture is blended for a few minutes, and then 636 g of sulphuric acid (98%) were added. The obtained mixture is kept in autoclave at 15 psi (over the atmospheric pressure) for 30 minutes at 121° C. After that, the aqueous phase is separated from the solid residue, by filtering on a filter. The solid phase, retained on the filter, is washed with 12.5 L of demineralised water, and the water coming from this washing operation is collected with the aqueous phase previously recovered. The aqueous phase, approximately 56 L, is then centrifuge refined to eliminate solid particles passed through the filter. After solid elimination, 52 L of crude aqueous extract, containing 141 g of hydroxytyrosol, with a HPLC purity of 50.5%, are obtained.

Then, crude aqueous extract, is loaded on a chromatographic column containing an acid activated ion exchange resin of the anionic type, previously activated by means of acetate cycle. For example, IRA-67 may be used. The liquid phase recovered at the end of the column, does not contain any hydroxytyrosol, which is instead continuously eluted with demineralised water until at least 90% of the initially charged hydroxytyrosol is recovered. The eluted phase coming from the first column is preferably charged on another chromatographic column containing an adsorption non-ionic resin. For example, resin XAD-1180 may be used. The liquid phase recovered at the end of this second column, does not contain any hydroxytyrosol. Then, hydroxytyrosol is eluted from the resin with demineralised water until at least 90% of the initially charged hydroxytyrosol is recovered.

The eluted phase contains approximately 114 g of hydroxytyrosol with an HPLC purity of about 96.7%.

Then, a 461 L fraction of purified extract containing 114 g of hydroxytyrosol obtained in a pilot plant is concentrated using a reverse osmosis pilot plant, equipped with a 2.5 m$^2$ polymeric membrane, in order to reduce the volume to 10 l of concentrate product. A 0.35 m$^2$ membrane made of the same material is then used, in order to obtain a hydroxytyrosol concentrate containing 3.5% of hydroxytyrosol. Finally the RO concentrate is rotaevaporated at 78° C. under a vacuum pressure of 245 mbar to allow about 10 times concentration of the olive fruit extract in liquid form reaching an hydroxytyrosol final concentration of 37.2% (w/w) with an HPLC purity of 93.3%.

EXAMPLE 2

Preparation of Olive Fruit Extract Powder by Spray-Drying

A sample of 260 ml of purified olive extract in liquid form containing 19.5 g of hydroxytyrosol obtained according to Example 1, is slowly stirred with 58 g of maltodextrin previously dissolved in 260 ml of demineralised water. For example, potato maltodextrin may be used. A peristaltic pump is used to feed the spray-dryer, which is previously equilibrated with an inlet air temperature of 150° C. The feeding speed is adjusted in order to obtain an outlet air temperature which is less than 100° C. 76 g of a white powder, with a moisture of 5.4% (Karl Fischer) and a hydroxytyrosol richness of 21.9% (w/w), are obtained.

EXAMPLE 3

Preparation of a Fortified Extra Virgin Olive Oil with Olive Fruit Extract

A sample of purified olive extract in liquid form containing a concentration of 40.6% (w/w) hydroxytyrosol obtained with a process according to Example 1, is selected for the fortification of a extra virgin olive oil. 6 samples, 400 g each, of such extra virgin olive oil were prepared. Increasing quantities of olive extract in liquid form are added in the weight ratio desired to the extra virgin olive oil and completely mixed, under very controlled parameters of temperature and agitation during 1 h. After that, stirring was switched off and mixture was filled into a decantation funnel and let settle down for 72 h. Then, the olive extract in excess has formed a bottom layer that is separated from the oil top phase to obtain the fortified extra virgin olive oil.

Straight afterwards, an aliquot of every one of the 6 samples of fortified extra virgin olive oil were used to measure antioxidant capacity (radical ABTS absorption capacity measured at 734 nm using Trolox as standard) and hydroxytyrosol content by HPLC. When results were plotted (see FIG. 1) as antioxidant capacity vs. concentration of hydroxytyrosol a linear correlation was obtained. Concretely antioxidant capacity of the non-fortified extra virgin olive oil was 0.24 mM Trolox equivalent per gram and antioxidant capacity of the fortified extra virgin olive oil with the highest weight ratio used in this example was 5.05 mM Trolox equivalent per gram, meaning that a 21 fold increase in the antioxidant capacity of the extra virgin olive oil was obtained.

EXAMPLE 4

Preparation of Fortified Sunflower Oil with Olive Fruit Extract

A sample of purified olive extract in liquid form containing a concentration of 40.6% (w/w) hydroxytyrosol obtained with a process according to Example 1, is selected for the fortification of a sunflower oil. 6 samples, 400 g each, of such sunflower oil were prepared. Increasing quantities of olive extract in liquid form are added in the weight ratio desired to the sunflower oil and completely mixed, under very controlled parameters of temperature and agitation during 1 h. After that, stirring was switched off and mixture was filled into a decantation funnel and let settle down for 72 h. Then, the olive extract in excess has formed a bottom layer that is separated from the oil top phase to obtain the fortified sunflower oil.

Figure 2:
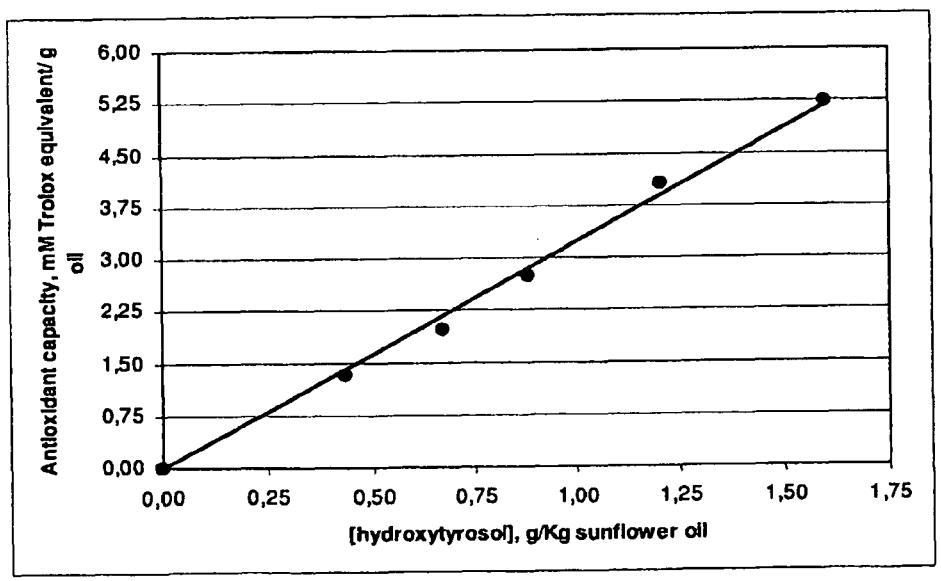

Straight afterwards, an aliquot of every one of the 6 samples of fortified sunflower oil were used to measure antioxidant capacity (radical ABTS absorption capacity measured at 734 nm using Trolox as standard) and hydroxytyrosol content by HPLC. When results were plotted (see FIG. 2) as antioxidant capacity vs. concentration of hydroxytyrosol a linear correlation was obtained. Concretely antioxidant capacity of the non-fortified sunflower oil was 0 mM Trolox equivalent per gram and antioxidant capacity of the fortified sunflower oil with the highest weight ratio used in this example was 5.42 mM Trolox equivalent per gram.

EXAMPLE 5

Preparation of a Fortified Corn Oil with Olive Fruit Extract

A sample of purified olive extract in liquid form containing a concentration of 40.6% (w/w) hydroxytyrosol obtained according to Example 1, is selected for the fortification of a corn oil. 6 samples, 400 g each, of such corn oil were prepared. Increasing quantities of olive extract in liquid form are added in the weight ratio desired to the corn oil and completely mixed, under very controlled parameters of temperature and agitation during 1 h. After that, stirring was switched off and mixture was filled into a decantation funnel and let settle down for 72 h. Then, the olive extract in excess has formed a bottom layer that is separated from the oil top phase to obtain the fortified corn oil.

Figure 3:
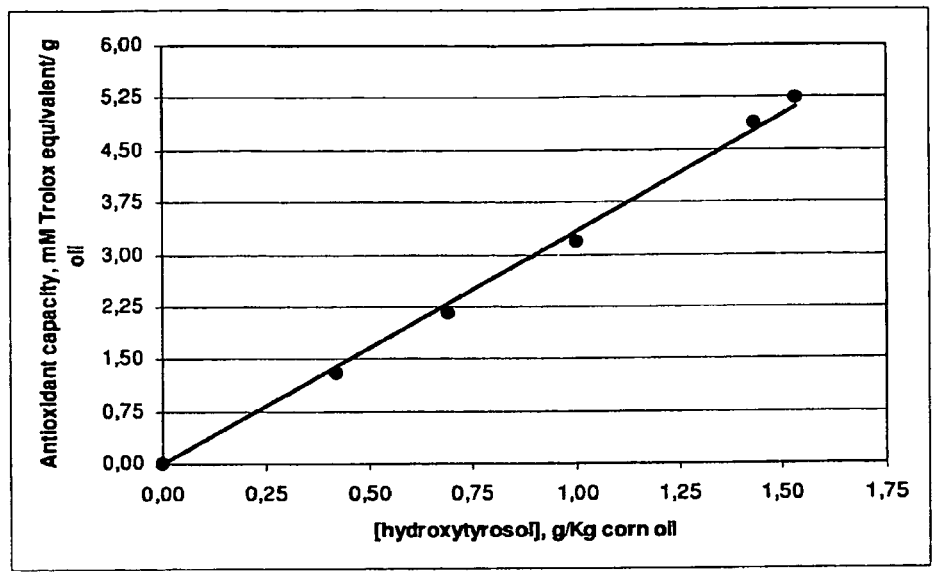

Straight afterwards, an aliquot of every one of the 6 samples of fortified corn oil were used to measure antioxidant capacity (radical ABTS absorption capacity measured at 734 nm using Trolox as standard) and hydroxytyrosol content by HPLC. When results were plotted (see FIG. 3) as antioxidant capacity vs. concentration of hydroxytyrosol a linear correlation was obtained. Concretely antioxidant capacity of the non-fortified corn oil was 0 mM Trolox equivalent per gram and antioxidant capacity of the fortified corn oil with the highest weight ratio used in this example was 5.23 mM Trolox equivalent per gram.

EXAMPLE 6

Preparation of Fortified Margarine with Olive Fruit Extract

A sample of purified olive extract in solid form containing a concentration of 23.3% (w/w) hydroxytyrosol obtained according to Example 2, is selected for the fortification of margarine. 6 samples, 200 g each, of such margarine were prepared as follow. Increasing quantities of olive extract in solid form are added in the weight ratio desired to the water phase together the other normal ingredients of margarine (whey, brine, etc.). Then water phase and refined oil blended with emulsifiers (lecithin) were blended together at temperatures around 50-60° C. while being slightly mixed. Finally, the mixed spread was chilled to make it go solid.

Figure 4:
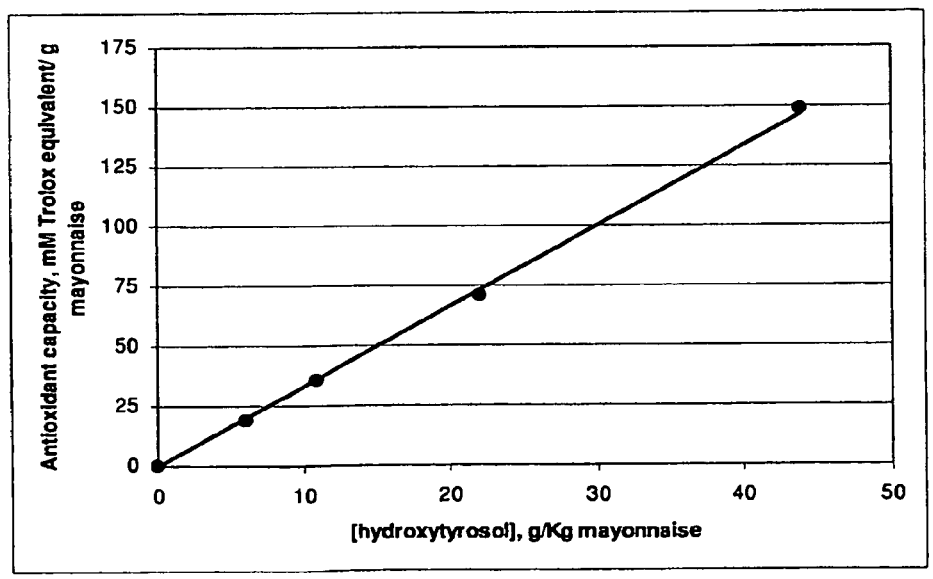

Straight afterwards, an aliquot of every one of the 6 samples of fortified margarine were used to measure antioxidant capacity (radical ABTS absorption capacity measured at 734 nm, using Trolox as standard) and hydroxytyrosol content by HPLC. When results were plotted (see FIG. 4) as antioxidant capacity vs. concentration of hydroxytyrosol a linear correlation was obtained. Concretely antioxidant capacity of the non-fortified margarine was 0 mM Trolox equivalent per gram and antioxidant capacity of the fortified margarine with the highest weight ratio used in this example was 189.05 mM Trolox equivalent per gram.

EXAMPLE 7

Preparation of a Fortified Mayonnaise with Olive Fruit Extract

Figure 5:
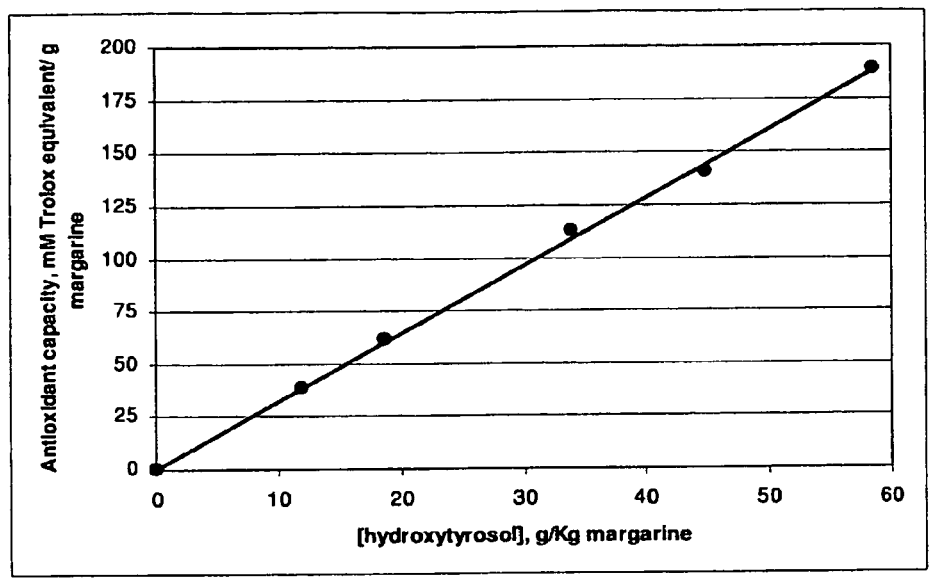

A sample of purified olive extract in solid form containing a concentration of 23.3% (w/w) hydroxytyrosol obtained according to Example 2, is selected for the fortification of a mayonnaise. 5 samples, 400 g each, of such mayonnaise were prepared as follows. Firstly, the egg yolks were added to the mixing bowl and blend thoroughly at speed 3. In a separate container blend the olive extract (increasing quantities of olive extract in solid form are added according to the weight ratio desired to the water phase), distilled water, lemon juice, vinegar, and salt. Stir until the olive extract is dissolved. Add this mixture to the egg yolks and blend at speed 3 for about 2 to 3 minutes. Finally, slowly add the oil and increase speed to 6, to make it go emulsion. Straight afterwards, an aliquot of every one of the 5 samples of fortified mayonnaise were used to measure antioxidant capacity (radical ABTS absorption capacity measured at 734 nm, using Trolox as standard) and hydroxytyrosol content by HPLC. When results were plotted (see FIG. 5) as antioxidant capacity vs. concentration of hydroxytyrosol a linear correlation was obtained. Concretely antioxidant capacity of the non-fortified mayonnaise was 0 mM Trolox equivalent per gram and antioxidant capacity of the fortified mayonnaise with the highest weight ratio used in this example was 148.33 mM Trolox equivalent per gram.

EXAMPLE 8

Preparation of a Fortified Extra Virgin Olive Oil by Emulsifying Olive Fruit Extract Using a Homogeniser A sample of purified olive extract in liquid form containing a concentration of 31.1% (w/w) hydroxytyrosol obtained with a process according to Example 1, is selected for the fortification of an extra virgin olive oil. 3 samples, 1000 g each, of such fortified extra virgin olive oil were prepared according the experimental design shown in the following Table 1:

TABLE 1

| Olive extract amount, µL olive extract/L oil | Total pressure, bar $1^{st}$ stage/$2^{nd}$ stage | Remarks |
|---|---|---|
| 230 | No | (Control without homogeniser) |
| 230 | 300/30 | |
| 230 | 500/30 | |

The content of an extra virgin olive oil bottle of 1 L, was poured, into a vessel and the stirring was switched on. Then, 230 microlitres of olive extract in liquid form is added to the oil and mixed by gentle stirring at 100 rpm. After 30 minutes a pre-emulsion has been formed. The pre-emulsion is feed into the feeding hopper of the homogeniser operating according to a double homogenization stages procedure. The homogenization of the pre-emulsion allows to obtain a stable emulsion.

Figure 6:
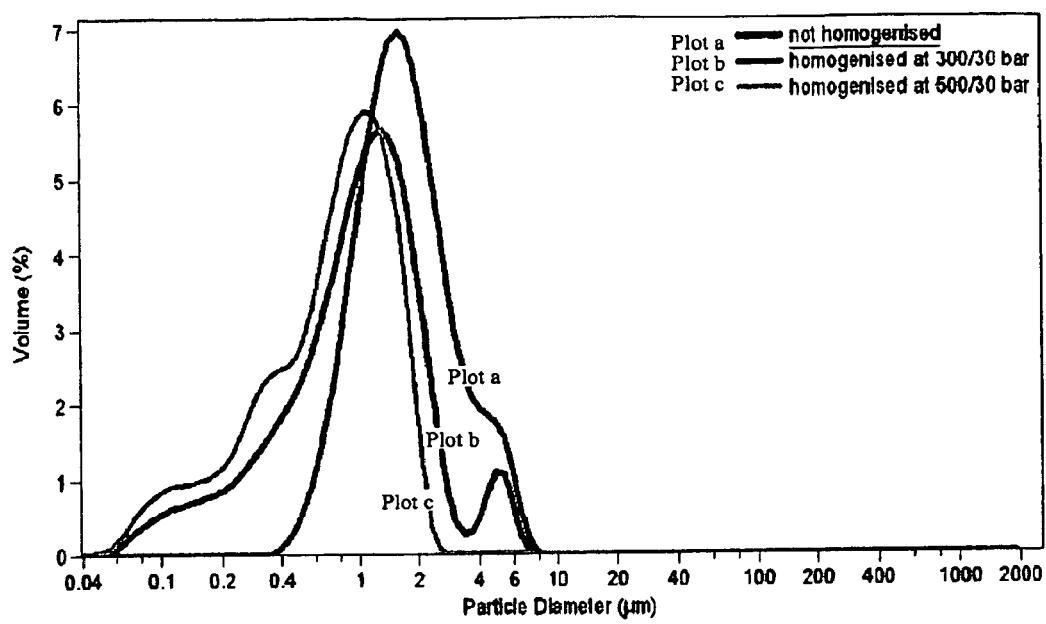
FIG. 6 is a graph comparing the particle size distribution curves of emulsions of liquid olive extract and extra virgin olive oil, prepared with or without use of a homogeniser.

Straight afterwards, an aliquot of each of the 3 samples of fortified extra virgin olive oil were used to measure homogenisation efficiency by laser particle size analyser, and hydroxytyrosol content was measured by HPLC. Particle size distribution curves were plotted (see FIG. 6) and average particle size was calculated. Results were summarized in the following Table 2:

TABLE 2

| Sample | [hydroxytyrosol], ppm | Average particle size, µm |
|---|---|---|
| Not homogenised | 51 | 1.999 |
| 300/30 | 60 | 1.259 |
| 500/30 | 59 | 0.849 |

Taking into account the particle size distribution curves (FIG. 6), the average particle size and the content of hydroxytyrosol (table 2), it can be concluded that the homogenisation technology is very well performing, allowing the preparation of stable microemulsions of liquid olive extract into oils for example when homogenising the pre-emulsion at 500/30 bar.

EXAMPLE 9

Preparation of Softgel Capsules of Fortified Extra Virgin Olive Oil with Olive Fruit Extract A sample of purified olive extract in liquid form containing a concentration of 35.6% (w/w) hydroxytyrosol obtained with a process according to Example 1, is selected for the fortification of an extra virgin olive oil.

The content of an extra virgin olive oil bottle of 1 L, was poured, into a vessel and the stirring was switched on. Then, 4.68 g of olive extract in liquid form is added to the oil and mixed by gentle stirring at 100 rpm. After 30 minutes a pre-emulsion has been formed. The pre-emulsion is feed into the feeding hopper of the homogeniser operating at 10 L/h and 500 bar for the first homogenization stage and 30 bar for the second homogenization stage.

The prepared emulsion was then encapsulated with an edible gelatin containing glycerin, water, titanium dioxide as masking agent and a colouring agent. The capsule shape used was oblong. The capsules were dried for two days at room temperature before packaging.

The creation and commercial manufacture of softgel capsules is well know in the art, and is not described in detail herein. Softgel capsules of fortified extra virgin olive oil with olive fruit extract according to the invention, can thus be prepared accordingly.

EXAMPLE 10

Use of Fortified Extra Virgin Olive Oil with Olive Fruit Extract in the Prevention or Treatment of Cardiovascular Diseases 10.1. Animals Forty-eight male Sprage Dawley rats (weight aprox. 150-180 g) were obtained from Harlan Interfauna Iberica SA (Barcelona, Spain) and maintained during all the experiment in the installations of the animalary service at the University of Murcia. The animals were randomly distributed into six experimental groups of 8 rats each one, and every 4 rats subgroup housed under standard conditions of lighting (day/night cycles of 12 h), temperature (22±2° C.) and humidity (60%).

10.2. Diets

The diets used in the study were as follows:
CONTROL DIET (C): 97% standard rat diet (Panlab) added with 3% refined sunflower oil.
ATHEROGENIC DIET (A): 95.5% standard rat diet (Panlab) added with 1.5% of cholesterol (Aldrich) and 3% of lard to induce atherosclerosis.
EXTRA VIRGIN OLIVE OIL (evoo) (O): 97% standard rat diet (Panlab) added with 3% extra virgin olive oil (evoo) whose natural content of hydroxytyrosol (HT) was determined, resulting in 5.7 mg HT/kg evoo.
STANDARD+ORALLY GAVAGE (5 mg HT/Kg (BW)) OF FORTIFIED EXTRA VIRGIN OLIVE OIL (G5): standard rat diet (Panlab) plus oral gavage of fortified extra virgin olive oil (prepared according to example 3 of the present invention). The precise amount of fortified extra virgin olive oil was administered by oral gavages every day in order to supply to every rat 5 milligram of hydroxytyrosol (HT)/kg of body weight (BW).
STANDARD+ORALLY GAVAGE (8 mg HT/Kg (BW)) OF FORTIFIED EXTRA VIRGIN OLIVE OIL (G8): standard rat diet (Panlab) plus oral gavage of fortified extra virgin olive oil (prepared according to example 3 of the present invention). The precise amount of fortified extra virgin olive oil contained 8 milligram of hydroxytyrosol (HT)/kg of body weight (BW) and was administered by oral gavages every day in order to supply to every rat 8 milligram of hydroxytyrosol (HT)/kg of body weight (BW)

Drinking water and food were available ad libitum. Nevertheless, throughout the study the average food supply for each animal was standardised to 30 g/day (real food intake per animal was unknown). Additionally, the precise amount of fortified extra virgin olive oil (fortified evoo) was administered by oral gavages to animal groups undertaking G5 and G8 diets in order to supply 5 and 8 milligram of HT/kg of body weight (BW), respectively, every day. To avoid fat oxidation, all diets were prepared daily by mixing the right quantities of standard rat diet (Panlab) and fats/oils and kept at 4° C. in the dark until use, and the non-consumed diet of past day was removed.

The concentrations of hydroxytyrosol (HT) in the O, G5 and G8 diets used in the study were measured by high performance liquid chromatography (HPLC).

10.3. Experimental Design

The experimental design is shown in the following Table 3:

TABLE 3

| GROUP | From day 1 to 30 | From day 31 to 60 | Remarks |
|---|---|---|---|
| 1 | Diet C | Diet C | Resulting diet: CC (Control diet) |
| 2 | Diet A | Diet A | Resulting diet: AA (Atherogenic diet-negative control) |
| 3 | Diet A | Diet C | Resulting diet: AC (effect of the control diet following an atherogenic diet) |
| 4 | Diet A | Diet O | Resulting diet: AO (effect of the evoo diet which naturally comprises 5.7 mg HT/kg evoo following an atherogenic diet) |
| 5 | Diet A | Diet G5 | Resulting diet: AG5 (effect of the fortified evoo diet, which results in a daily intake of 5 mg HT/kg (BW), following an atherogenic diet) |
| 6 | Diet A | Diet G8 | Resulting diet: AG8 (effect of the fortified evoo diet, which results in a daily intake of 8 mg HT/kg (BW), following an atherogenic diet) |

Animal groups treated with CC, AA, AC, AO, AG5 and AG8 diets were fed as follows.

Animal groups treated with CC or AA diets, respectively, have been fed for 2-months with diets C or A.

Animal group treated with AC diet has been fed for 1-month with the A-diet (atherogenic diet, negative control) followed by a further month with diet C (where only standard rat diet (Panlab) was given with no addition of any sunflower oil).

Animal group treated with AO diet has been fed for 1-month with the A-diet (atherogenic diet, negative control) followed by a further month with diet O (evoo diet, which naturally comprises 5.7 mg HT/kg evoo).

Animal group treated with G5 diet has been fed for 1-month with the A-diet (atherogenic diet, negative control) followed by a further month with diet G5 (fortified evoo diet, which results in a daily intake of 5 mg HT/kg (BW), supplied by oral gavage.

Animal group treated with G8 diet has been fed for 1-month with the A-diet (atherogenic diet, negative control) followed by a further month with diet G8 (fortified evoo diet, which results in a daily intake of 8 mg HT/kg (BW) supplied by oral gavage.

At the end of the experiment, fasted animals were anesthetized and immediately after euthanasia intra-cardiac punction was made to collect blood in tubes. Plasma was separated by centrifugation for analysis.

10.4. Determination of Lipids, and Total Antioxidant Capacity (TAC) in Plasma.

The plasma concentrations of total cholesterol (TC), HDL-cholesterol (HDL-C) and triglycerides (TG) were determined by colorimetry using commercial kits purchased from Biosystems (Barcelona, Spain) according to the manufacturers instructions.

The TAC of plasma was measured as described by Re et al (1999) using Trolox as standard. Fresh plasma was diluted in PBS and 20 microL were incubated in the dark with 980 microL of ABTS+ [2,2-Azino-bis(3-ethylbenzthiazoline-6-sulfonic acid)] radical cation for 10 min at room temperature. After 10 minutes, absorbance was read at 734 nm. ABTS+ cation mother solution was prepared by addition of 440 microL of 14 mM potassium persulfate in water to 25 mL of a 7 mM solution of ABTS (Sigma A-1808) in water and incubation for 12-14 h in the dark. The working solution was obtained by dilution of the mother solution with PBS until the absorbance at 734 nm was 0.7±0.02.

10.5. Statistical Analysis

The data are expressed as means+standard error of the means (S.E.M.), and were analyzed by one-way ANOVA. Differences between the groups were assessed by the Tukey test. Differences were considered significant when P-values were <0.05. The data was analysed using Sigma Stat software (Version 2.03).

10.6. Discussion.

Figure 7:
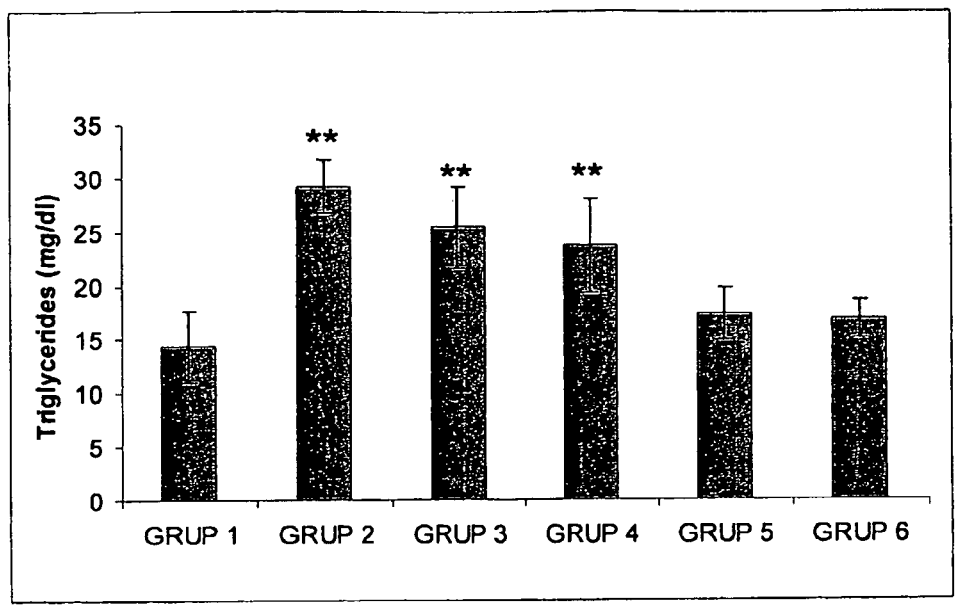
FIGS. 7-9, are graphs showing the effects of fortified extra virgin olive oil with olive extract according to the present invention, on rat triglycerides, atherogenic index (total cholesterol/HDL cholesterol) and total antioxidant capacity in plasma (TAC), respectively.
Figure 8:
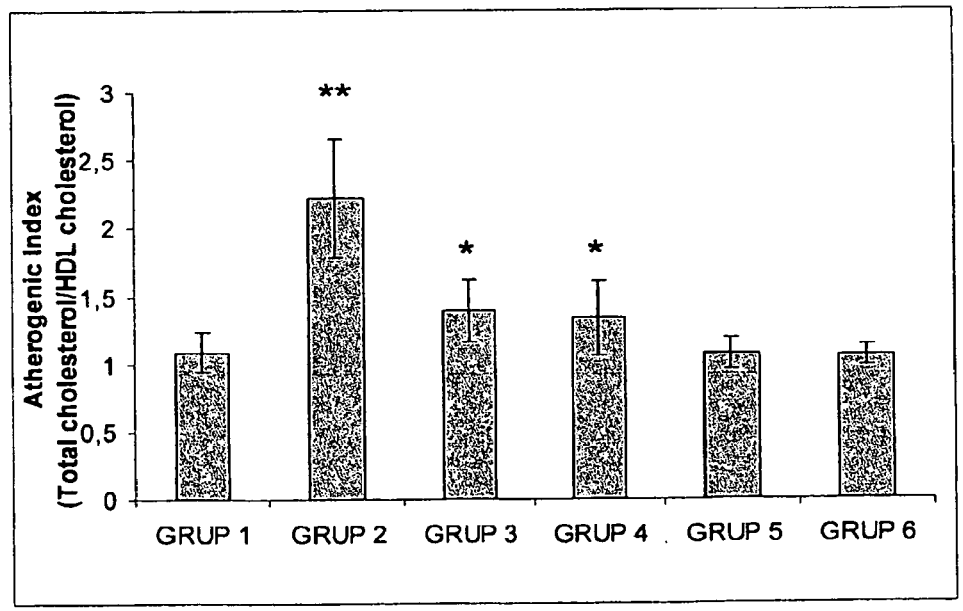
Figure 9:
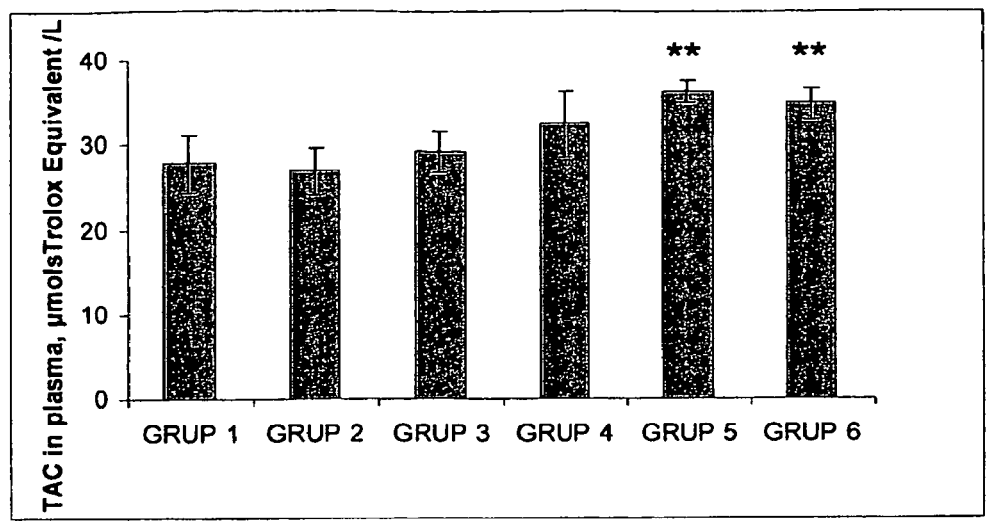

The obtained results are shown in the enclosed FIGS. 7 to 9, where the triglycerides levels, atherogenic index and total antioxidant capacity (TAC) have been correlated with different animal groups.

FIG. 7 shows the correlation between the triglycerides levels and the animals, divided according to the different diet schemes. According to said Figure, animal group 1 treated with CC diet (control diet) shows the lowest triglycerides levels, while animal group 2, treated with AA diet (atherogenic diet—negative control) shows the highest, being statistically significant the difference of the triglycerides levels between groups 1 and 2 with a P-value <0.001. An interesting result is shown according to animal groups 5 and 6, that were treated with G5 and G8 diets respectively. The triglycerides values show that, even if the animals were fed with an atherogenic diet for the first month, in the subsequent month of treatment, where they were fed with a standard diet plus and oral gavage of fortified extra virgin olive oil according to the present invention, no statistically significant difference of the triglycerides level between groups 5 and 1 or 6 and 1 were observed. In other words, after the month of treatment with the atherogenic diet a significant reduction of the triglycerides levels to a value that is comparable to the level obtained with the control diet, was observed for animal groups G5 and G8. The same effect was not observed when only extra virgin olive oil (evoo) was given to the animals in addition to a standard diet in the month following the month of treatment with the atherogenic diet (animal group 4). In this case, triglycerides level (even though lower than those of negative control group 2), resulted in a statistically significant difference with respect to the triglycerides level detected for the animals fed with the control diet (group 1) with a P-value <0.001. In addition, statistically significant difference at the triglycerides level between groups 3 and 1 were observed, with a P-value <0.001, meaning that the effect of non fortified extra virgin olive oil (G4) are not significantly better than those of a standard diet, after one month of atherogenic diet (G3).

FIG. 8 shows the correlation between the atherogenic index and the animals, divided according to the different diet schemes. According to said Figure, animal group 1 treated with CC diet (control diet) shows the lowest atherogenic index value, while animal group 2, treated with AA diet (atherogenic diet—negative control) shows the highest, being statistically significant the difference of the atherogenic index value between groups 1 and 2 with a P-value <0.001. An interesting result is shown according to animal groups 5 and 6, that were treated with G5 and G8 diets respectively. No statistically significant difference of the atherogenic index value between groups 5 and 1 or 6 and 1 were observed. In other words after the month of treatment with the atherogenic diet a significant reduction of the atherogenic index value to a value that is comparable to the level obtained with the control diet, was observed for animal groups G5 and G8. By the contrary, the same effect was not observed when only extra virgin olive oil (evoo) was given to the animals in addition to a standard diet in the month following the month of treatment with the atherogenic diet (animal group 4). In this case, atherogenic index value (even though being statistically significant the difference with those of negative control group 2), resulted in a statistically significant difference with respect to the atherogenic index value detected for the animals fed with the control diet (group 1) with a P-value <0.05. The atherogenic index levels derived from animal groups 5 and 6 suggest a possible synergic effect due to the fortified extra virgin olive oil according to the present invention.

FIG. 9 shows the correlation between TAC plasma values and the animals, divided according to the different diet schemes. According to said Figure, animal groups 5 and 6 show the highest Total Antioxidant Capacity, being statistically significant the difference of the TAC value between groups 5 and 1 (P-value <0.001) and 6 and 1 (P-value <0.001). This result again confirms that the fortified oil/oil-containing product according to the present invention, and particularly fortified extra virgin olive oil, presents several advantages and can be used in the protection of the cardiovascular system.

In fact, high cholesterol/triglycerides levels, low HDL cholesterol levels and specially oxidised LDLs are among risk factors associated with atherosclerotic plaque builds up in the arteries and metabolic syndrome. Summarizing the above results, studies were carried out on the effect that a fortified nutritional product containing an olive extract has on biomarkers for cardiovascular events, and the obtained results were compared with the results obtained with similar nutritional products in the absence of fortification with the olive extract according to the present invention. Taking all the parameters measured into account (see FIGS. 7 to 9), it can be concluded that the components of the fortified nutritional product (containing the olive extract) show a synergic effect. It can also be concluded that the regular administration of the fortified nutritional product (containing the olive extract according to the present invention) protects the cardiovascular system which, to a greater or lesser extent, prevents the occurrence of adverse cardiovascular events and therefore may well be considered as a health promoting nutritional product.

EXAMPLE 11

Use of Fortified Extra Virgin Olive Oil (Evoo Added with the Olive Extract According to the Invention) in the Treatment of Hypertension 11.1. Animals Thirty-six male Sprage Dawley rats (weight aprox. 200 at the beginning of the experiment) were obtained from Harlan Interfauna Iberica SA (Barcelona, Spain) and maintained during all the experiment in the installations of the animalary service at the University of Murcia. The animals were randomly distributed into six experimental groups of 6 rats each one, housed under standard conditions of lighting (day/night cycles of 12 h), temperature (22±2° C.) and humidity (60%).

11.2. Diet

During the setting period and the experimental periods, rats were feed on a solid standard diet for rats (Panlab). Drinking water and food were available ad libitum. After an setting period of 7 days, treatments according the experimental design were started.

11.3. Experimental Design

In order to determine the effect of fortified extra virgin olive oil (evoo added with the olive extract according to the present invention) N-nitro-L-arginine-methylester (L-NAME) induced hypertension model was used.

After the setting period, but before the starting of L-NAME induced hypertension treatment, basal recordings of arterial blood pressure (D0) were measured with a Letica 5002 equipment.

Animals were treated according to an experimental design as showed in the following table 4:

TABLE 4

| GROUP | Drinking water with L-NAME* | Oral gavages | Remarks |
|---|---|---|---|
| 1 | No | No | No hypertension induced |
| 2 | 40 mg L-NAME/Kg* | No | Hypertension induced (negative control) |
| 3 | 40 mg L-NAME/Kg* | 0.2 ml of extra virgin olive oil (evoo) | Induced hypertension in parallel with the administration of extra virgin olive oil (evoo) naturally containing 5.7 ppm of HT/Kg evoo |
| 4 | 40 mg L-NAME/Kg* | 0.2 mL of fortified evoo that was added with the olive extract according to the invention, thus resulting in a daily intake of 5 mg HT/Kg BW | Induced hypertension in parallel with the administration of fortified evoo, which results in a daily intake of 5 mg/kg (BW) of HT |
| 5 | 40 mg L-NAME/Kg* | 0.2 mL of fortified evoo that was added with the olive extract according to the invention, thus resulting in a daily intake of 8 mg HT/Kg BW | Induced hypertension in parallel with the administration of fortified evoo, which results in a daily intake of 8 mg HT/kg (BW) |
| 6 | 40 mg L-NAME/Kg* | 100 mg Captopril/Kg | Positive control: Induced hypertension in parallel with the administration of 100 mg of Captopril (blood pressure lowering agent) |

*L-NAME treatment was administered to all groups through drinking water intake, available ad libitum, taking into consideration a body weight of 200 g per animal and standardising the average drinking water supply for animal to 40 mL/day (real drinking water intake per animal was unknown).

11.4. Cronogramme of Activities

In order to achieve rats to be in the habit, measurements of arterial blood pressure using the recording of pulsations of the tail artery with a Letica 5002 equipment were made during the setting period.

Cronogramme of experimental measurements/treatments were summarized in the following table 5:

TABLE 5

| Day | Measurements of arterial blood pressure | Drinking water supplemented with L-NAME | Oral gavages |
|---|---|---|---|
| 0 | Yes | Yes | No |
| 1 | No | Yes | Yes |
| 2 | Yes | Yes | Yes |
| 3 | No | Yes | Yes |
| 4 | Yes | Yes | Yes |
| 5 | No | Yes | Yes |
| 6 | No | Yes | Yes |
| 7 | Yes | Yes | Yes |

11.5. Determination of Arterial Blood Pressure.

Arterial blood pressure was measured with a periodicity according the above cronogramme, by the tail-cuff method. Before the measurement, rats were kept at 37° C. for 10 min to make the pulsations of the tail artery detectable. The equipment used in the present study, LE 5002 (Letica, Hospitalet, Barcelona, Spain), has a high sensitivity pulse transducer coupled with an accurate microprocessor program, and allow accurate measurements of arterial blood pressure. The arterial blood pressure measurements were performed at the same time of the day in order to avoid any influence of the circadian cycle.

11.6. Statistical Analysis

The data are expressed as means±standard error of the means (S.E.M.), and were analyzed using Sigma Stat software (Version 2.03).

11.7. Discussion.

Figure 10:
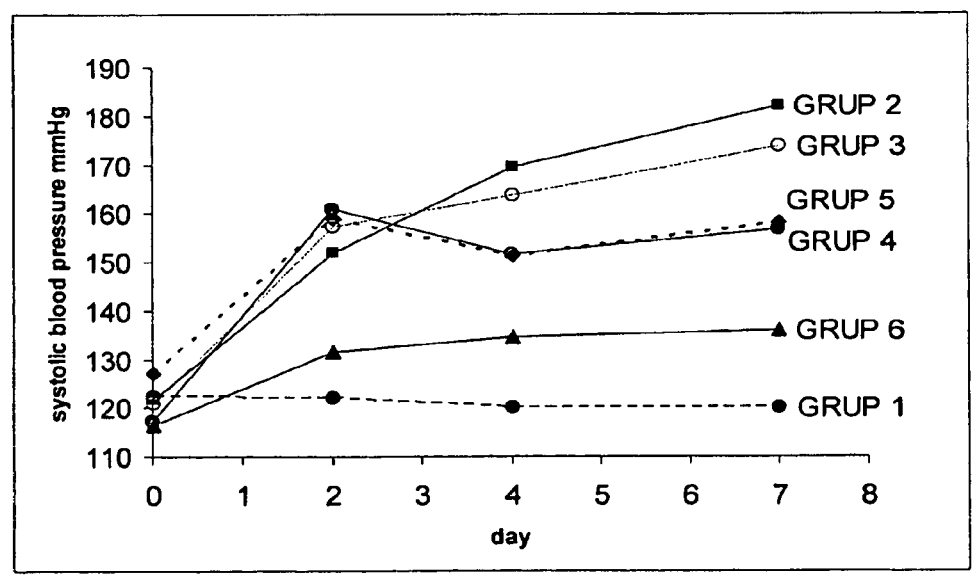
FIG. 10 is a graph showing the effect of fortified extra virgin olive oil with olive extract according to the present invention, on rat systolic blood pressure.

FIG. 10 shows the correlation between the detected blood pressure values and the animals, divided according to the different treatment schemes. According to said Figure, animal group 1 showed no hypertension, while animal group 2 showed high and increasing blood pressure values, induced by L-NAME treatment. Animal group 6 (positive control), in unison with L-NAME hypertension induction, was treated with Captopril, a known and highly efficient blood pressure lowering agent, and shown a significant reduction of the blood pressure values. Animal group 3, in unison with L-NAME hypertension induction, was treated with extra virgin olive oil (evoo) while animal groups 4 and 5, in unison with L-NAME hypertension induction, were treated with fortified extra virgin olive oil (fortified evoo). Animal group 4 and 5 blood pressure levels were significantly lower than animal group 3 blood pressure levels, thus resulting in a better action on hypertension exploited by the fortified extra virgin olive oil according to the present invention with respect to the action exploited by non-fortified evoo.

The above indicated results are very interesting, as arterial hypertension is among risk factors associated with atherosclerotic plaque builds up in the arteries and metabolic syndrome. The effect that fortified extra virgin olive oil with olive extract according to the present invention has on arterial blood pressure have been studied, and compared with control groups that didn't undergo to treatment with olive extract. Taking into account the systolic blood pressure measurements (FIG. 10), it can be concluded that olive extract, and the regular administration of the nutritional product containing an olive extract according to the invention, show antihypertensive activity which, to a greater or lesser extent, prevents the occurrence of cardiovascular events. The nutritional product containing an olive extract according to the invention therefore, may well be considered as a health promoting dietary supplement and may be a successful strategy to produce functional foods, like fortified extra virgin olive oil with antihypertensive activity.

EXAMPLE 12

Use of Olive Fruit Extract Rich in Highly Pure Hydroxytyrosol in the Prevention or Treatment of Cardiovascular Diseases 12.1. Animals Thirty two male Sprage Dawley rats (weight aprox. 150-180 g) were obtained from Harlan Interfauna Iberica SA (Barcelona, Spain) and maintained during all the experiment in the installations of the animalary service at the University of Murcia. The animals were randomly distributed into four experimental groups of 8 rats each one, and every 4 rats subgroup housed under standard conditions of lighting (day/night cycles of 12 h), temperature (22±2° C.) and humidity (60%).

12.2. Diets

The diets used in this study were as follows:

CONTROL DIET (C): 97% standard rat diet (Panlab) added with 3% refined sunflower oil.

ATHEROGENIC DIET (A): 95.5% standard rat diet (Panlab) added with 1.5% of cholesterol (Aldrich) and 3% of lard to induce atherosclerosis.

ATHEROGENIC DIET+ORALLY GAVAGE (8 mg HT/Kg (BW)) OF HYDROXYTYROSOL (A-G8): 95.5% standard rat diet (Panlab) added with 1.5% of cholesterol (Aldrich) and 3% of lard to induce atherosclerosis plus oral gavage hydroxitirosol extract (8 milligram of hydroxytyrosol/kg of body weight) and was administered by oral gavages every day in order to supply to every rat 8 milligram of hydroxytyrosol (HT)/kg of body weight Drinking water and food were available ad libitum. Nevertheless, throughout the study the average food supply for each animal was standardised to 30 g/day (real food intake per animal was unknown). To avoid fat oxidation, all diets were prepared daily by mixing the right quantities of standard rat diet (Panlab) and fats/oils and kept at 4° C. in the dark until use, and the non-consumed diet of past day was removed.

The concentrations of hydroxytyrosol (HT) in the A-G8 diet used in the study were measured by high performance liquid chromatography (HPLC).

12.3. Experimental Design

The experimental design is shown in the following Table 6:

TABLE 6

| GROUP | From day 1 to 30 | From day 31 to 60 | Remarks |
|---|---|---|---|
| 1 | Diet C | Diet C | Resulting diet: CC (Control diet) |
| 2 | Diet A | Diet A | Resulting diet: AA (Atherogenic diet-negative control) |
| 3 | Diet A | Diet C | Resulting diet: AC (effect of the control diet following an atherogenic diet) |
| 4 | Diet A-G8 | Diet A-G8 | Resulting diet: AG8-AG8 (effect of the HT 8 mg/kg (BW), with an atherogenic diet) |

Animal groups treated with CC, AA, AC, and A-G8 diets were fed as follows.

Animal groups treated with CC or AA diets, respectively, have been fed for 2-months with diets C or A.

Animal group treated with AC diet has been fed for 1-month with the A-diet (atherogenic diet, negative control) followed by a further month with diet C (where only standard rat diet (Panlab) was given with no addition of any sunflower oil).

Animal group treated with AG8-AG8 diet has been fed for 2-month with the A-G8 (atherogenic diet plus gavage of 8 mg/kg HT)

At the end of the experiment, fasted animals were anesthetized and immediately after euthanasia intra-cardiac punction was made to collect blood in tubes. Plasma was separated by centrifugation for analysis.

12.4. Statistical Analysis

The data are expressed as means±standard error of the means (S.E.M.), and were analyzed by one-way ANOVA. Differences between the groups were assessed by the Tukey test. Differences were considered significant when P-values were <0.05. The data was analysed using Sigma Stat software (Version 2.03).

12.5. Discussion.

Figure 11:
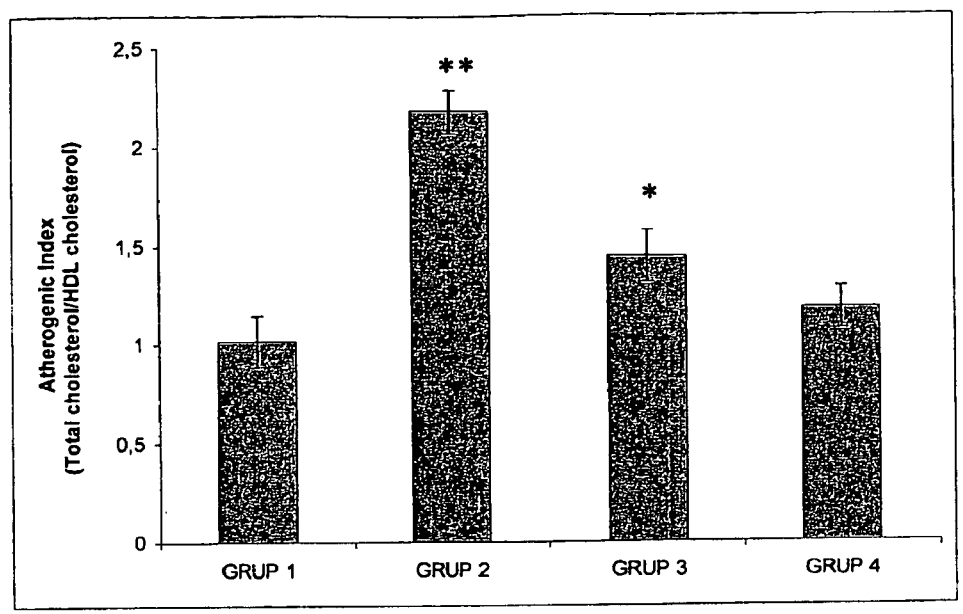
FIG. 11, is a graph showing the effects of olive fruit extract rich in highly pure hydroxytyrosol according to the present invention, on rat atherogenic index (total cholesterol/HDL cholesterol).

The obtained results are shown in the enclosed FIG. 11, where the atherogenic index has been correlated with different animal groups that, as already said, are indicated in Table 6.

FIG. 11 shows the correlation between the atherogenic index and the animals, divided according to the different diet schemes. According to said Figure, animal group 1 treated with CC diet (control diet) shows the lowest atherogenic index value, while animal group 2, treated with AA diet (atherogenic diet—negative control) shows the highest, being statistically significant the difference of the atherogenic index value between groups 1 and 2 with a P-value <0.001. An interesting result is shown according to animal group 4, that, in this experiment, were treated with A-G8 diet. No statistically significant difference of the atherogenic index value between group 4 and 1 was observed. In other words, after two month of treatment with the atherogenic diet plus a gavage of olive fruit extract rich in hydroxytyrosol, an unaltered atherogenic index value that is comparable to the level obtained with the control diet, was observed for animal groups A-G8. By the contrary, the same effect was not observed when only a standard rat diet was given to the animals of group 3 in the month following the first month of treatment with the atherogenic diet (animal group 3). In this case, atherogenic index value (even though being statistically significant the difference with those of negative control group 2), resulted in a statistically significant difference with respect to the atherogenic index value detected for the animals fed with the control diet (group 1) with a P-value <0.05. The atherogenic index level derived from animal group 4 suggest a preventive effect due to the olive fruit extract rich on hydroxytyrosol obtained according to the present invention.

Taking all the measured parameters into account, it can be concluded that the regular administration of the olive extract according to the present invention, protects the cardiovascular system which, to a greater or lesser extent, prevents the occurrence of some of the risk factors that are considered associated with atherosclerotic plaque builds up in the arteries and metabolic syndrome, and therefore may well be considered a health promoting natural extract, to be used in the preparation of dietary supplements.

As previously mentioned, the edible oil of the invention maintains the original organoleptic properties, i.e. there is no increase in bitterness value and no by-products of the hydrolysis of complex polyphenols (e.g. oleuropein, that is an ester of hydroxytyrosol) such as oleuropeina aglycone (e.g. aldehydic form of oleuropeina aglycon) and sugars (e.g glucose, that is the sugar present in the oleuropein).

The following is an explanation of the tests on quality normally carried out on oils, namely olive oils.

1) Acidity

The acidity expresses the percentage content (in weight) of the free fatty acids in the oil under examination. Free fatty acids are normally present also in oils obtained from sound olives: when the triglycerides are formed, there is a progressive increase in acidity due to the action of enzymes (lipase) naturally present in the fruit, which help the fatty acids to detach from the molecule of triglyceride (lipolisis). The same lipolitic phenomenon can be caused by enzymes produced by micro-organisms which grow on the fruit. Thus, in order to obtain a product which is organoleptically better and which has lower acidity, it is necessary to preserve the olives well in the store.

2) The peroxide Value

The content of peroxides in the oil under examination is expressed by the peroxide value. The higher the number, the greater is the degradation due to oxydation of the oil. In their turn the peroxides are subject to further oxydation which gives rise to the formation of other compounds which are determinable in different ways (aldehydes, ketones etc.) These compounds, called compounds of secondary oxydation, are responsible for making the oil rancid. Because of oxydation and due to the enzymes present in the tissue of the fruit (lipoxygenases), a certain concentration of peroxides is already present in the fruit before pressing. Particular natural circumstances (e.g. temperatures below freezing, dacic infestations, drought etc.), or olives incorrectly harvested and preserved may encourage a further formation of peroxides. Even during milling peroxides can increase greatly through bad processing or due to incorrect hygiene in the olive-press and/or of the vessels. Finally, prolonged exposure of the oil to light or heat sources is another cause of the increase of peroxides. They are determined through titration.

3) Spectrophotometric Investigation in Ultraviolet.

This test consists of measuring three parameters (K232, K270,ΔK) determined during the same analytic procedure. The greater the value of K232, the greater the concentration of conjugated dienes, whereas K270 is proportional to the concentration of conjugated trienes. However, compounds of oxydation of the conjugated dienes contribute to K232 while compounds of secondary oxydation (aldehydes, ketones etc.) contribute to K270.

It is for this reason that if the value of K270 exceeds the limit of the category to which the oil is believed to belong, EC regulations provide for a particular pre-treatment of the sample (with alumina) before a second spectrophotometric test. If the new value exceeds that limit, the oil must be declared not pure.

4) Bitterness Taste.

This test is carried out according to Gutierrez et al, J. Am. Oil. Chem. Soc. 1992, 69(4), 394-395, that found a linear correlation between absorbance at 225 nm (test K225) and the bitter taste of the oil.

Experience has shown that problems can arise for the oil's direct consumption when K225 value exceeds of 0.300 or more. In addition, K225 values of the order of 0.360 or higher correspond to quite bitter oils which are rejected by most of the consumers.

EXAMPLE 13

Comparative Example

Preparation of a Fortified Extra Virgin Olive Oil with Different Sources of Olive Polyphenols For comparative purposes, a sample of purified olive extract obtained with a process according to Example 1 and commercial samples of olive extract from olive leaf and from olive mill vegetation water were selected for the fortification of an extra virgin olive oil. The specifications of every extract are shown at the following Table C1:

TABLE C1

| Extract | [HT], % | [oleuropein], % | HT purity (by HPLC 280 nm) | Residual organic solvent, ppm. |
|---|---|---|---|---|
| purified olive extract (according Ex. 1) | 34.5 | N.D. | 93.4 | N.D. |
| Olive leaf extract | 0.4 | 35.6 | 5.2 | Ethanol: 156 ppm |
| Olive mill vegetation water | 2.5 | 0.2 | 51.3 | Acetone 105 ppm |

N.D.: non detected

A 3 L bottle of extra virgin olive oil (Hojiblanca) was obtained from supermarket and used for the different trials.

4 samples, 500 mL each, of such extra virgin olive oil were poured into glass beakers. And the different extracts were added according next table C2:

TABLE C2

| Extract | Weight of extract added, g | Maximum theoretical increase of [HT] in the oil, ppm. |
|---|---|---|
| A) purified olive extract (according Ex. 1) | 0.1 | 69 |
| B) Olive leaf extract | 20 | 160 |
| C) Olive mill vegetation water | 20 | 1000 |
| D) No extract addition (control) | — | — |

Then, every test A, B, C and D was carried out as follows:

A) 0.11 g of purified olive extract (according Ex.1) in liquid form is added to the 500 mL extra virgin olive oil sample and mixed by gentle stirring at 100 rpm. After 30 minutes a pre-emulsion has been formed. The pre-emulsion is feed into the feeding hopper of the homogeniser operating according to a double homogenization stages procedure. The homogenization of the pre-emulsion, operated at a pressure of 300/30, bar for $1^{st}$ stage/$2^{nd}$ stages respectively allows to obtain a stable emulsion.

B) 20 g of olive leaf extract was added to the 500 mL extra virgin olive oil sample and magnetically stirred during 2 h at 60° C. (for comparison with Ex. comparative 1 of IT1326553). After the heating treatment was completed the sample has a dark green colour and still contains a lot of solid material. Then, the solid is decanted and the oil cooled to room temperature, finally the sample was centrifuged to remove the solids.

C) 20 g of olive mill vegetation water extract was added to the 500 mL extra virgin olive oil sample and magnetically stirred during 2 h at 60° C. (for comparison with Ex. comparative 3 of IT1326553). After the heating treatment was completed the sample still contains a lot of solid material. Then, the solid is decanted and the oil cooled to room temperature, finally the sample was centrifuged to remove the solids.

Straight afterwards, an aliquot of every one of the 4 samples, 3 samples of fortified extra virgin olive oil (samples A; B and C) and 1 control sample of extra virgin olive oil (sample D), were used to measure bitter index (K225), measured according to Gutierrez et al, J. Am. Oil. Chem. Soc. 1992, 69(4), 394-395. and hydroxytyrosol and oleuropein content by HPLC. Results are summarized in the following Table C3:

TABLE C3

| Extract | K225 | [HT] in the oil, ppm. | [oleuropein] in the oil, ppm. | Yield of HT incorporation in the oil, % |
|---|---|---|---|---|
| A) purified olive extract (according Ex. 1) | 0.24 | 71 | N.D. | 92.8 |
| B) Olive leaf extract | 0.35 | 28 | 10 | 13.1 |
| C) Olive mill vegetation water | 0.32 | 38 | 1 | 3.1 |
| D) No extract addition (control) | 0.25 | 7 | N.D. | — |

The preliminary test referred to above table showed that the source and purity of the olive extract is critical to increase of the level of hydroxytyrosol while avoiding alteration of organoleptic properties of the oil, causing non-pleasant taste because of excessive bitterness and/or astringency.

Moreover, the use of olive leaf extracts and olive mill vegetation water extracts and the use of the above mentioned techniques (heating at 60° C. for 2 hours) according to IT patent 1326553, are too harsh, technically complex and not practical (a lot of solid extract remains in the oil after the treatment) or not economically feasible (very low content of hydroxytyrosol incorporated into the olive oil) for alimentary field. In addition the amount of hydroxytyrosol incorporated in the vegetable oil is too low to effectively protect LDL against oxidative modification to any important extent.

EXAMPLE 14

Comparative Example

Determination of Organoleptic Properties of Edible Oils Fortified with Different Extracts The samples A-C and the control according to Example 13 were tested for the following quality properties, summarized in table C4.

TABLE C4

| Extract | Free acidity, as % oleic acid NMT 0.8% | Peroxide Index, as meq $O_2$/Kg NMT 20. | K270, NMT 0.22. | K232, NMT 2.5. |
|---|---|---|---|---|
| A) purified olive extract (according Ex. 1) | 0.22 | 7 | 0.17 | 1.76 |
| B) Olive leaf extract | 0.35 | 9.5 | 0.27 | 2.13 |

TABLE C4-continued

| Extract | Free acidity, as % oleic acid NMT 0.8% | Peroxide Index, as meq O$_2$/ Kg NMT 20. | K270, NMT 0.22. | K232, NMT 2.5. |
|---|---|---|---|---|
| C) Olive mill vegetation water | 0.40 | 7.9 | 0.18 | 1.91 |
| D) No extract addition (control) | 0.22 | 7.2 | 0.15 | 1.85 |

Changes in quality parameters, namely free acidity value, peroxide value, K270 and K232 were found. The K270 value 0.27 for the olive oil fortified with olive leaf extracts is very high and exceeds the maximum value accepted for extra virgin olive oils according to Commission Regulation (EC) No 702/2007 of 21 Jun. 2007.

We claim:

1. A nutritional product, that is an edible oil, having a K225 value of 0.28 or less, characterized in that it has a content of at least 30 ppm of hydroxytyrosol and a content of aldehydic form of oleuropein aglycon of less than 120 ppm, wherein said hydroxytyrosol is dispersed in the oil as a stable aqueous emulsion.

2. The nutritional product according to claim 1 containing from 30 ppm to 300 ppm of hydroxytyrosol.

3. The nutritional product according to claim 1, containing from 300 ppm to 30000 ppm of hydroxytyrosol.

4. The nutritional product according to claim 3, that is a dietary supplement, in the form of a soft gel capsule that encapsulates an edible oil.

5. The nutritional product according to claim 1, wherein said oil is a vegetable oil selected from virgin olive oil, extra virgin olive oil, olive oil, lampante olive oil, refined olive oil, crude olive-pomace oil, refined olive-pomace oil, sunflower oil, corn oil, soya oil, flax seed oil, almond oil, canola oil, safflower oil, palm oil, coconut oil, rapeseed oil, or mixtures thereof.

6. The nutritional product according to claim 1, wherein said oil is a marine or fish oil obtained from algae, krill, menhaden, anchovy, tuna, herring, sardines, mackerel, cod, or mixtures thereof.

7. The nutritional product according to claim 1, which is a food product containing an edible oil and contains 30 ppm to 300 ppm of hydroxytyrosol.

8. The nutritional product according to claim 7 which is selected from margarine, mayonnaise, garlic mayonnaise, gazpacho soup, spreadable sauces and salad dressings.

9. The nutritional product according to claim 1 for the prevention or treatment of plaque build-up in the arteries.

10. A nutritional product, that is an edible oil, having a K225 value of 0.28 or less, characterized in that it has a content of at least 30 ppm of hydroxytyrosol and a content of aldehydic form of oleuropein aglycon of less than 120 ppm and wherein said product is free from EtOH and MeOH.

11. The nutritional product according to claim 10 containing from 30 ppm to 300 ppm of hydroxytyrosol.

12. The nutritional product according to claim 10 containing from 300 ppm to 30000 ppm of hydroxytyrosol.

13. The nutritional product according to claim 10, containing from 300 ppm to 30000 ppm of hydroxytyrosol that is a dietary supplement, in the form of a soft gel capsule that encapsulates an edible oil.

14. A nutritional product, that is an edible oil, having a K225 value of 0.28 or less, characterized in that it has a content of at least 30 ppm of hydroxytyrosol and a content of aldehydic form of oleuropein aglycon of less than 120 ppm and wherein said product is free from organic solvents.

15. The nutritional product according to claim 14, containing from 30 ppm to 3000 ppm of hydroxytyrosol.

16. The nutritional product according to claim 14, containing from 300 ppm to 30000 ppm of hydroxytyrosol.

17. The nutritional product according to claim 14, containing from 300 ppm to 30000 ppm of hydroxytyrosol that is a dietary supplement, in the form of a soft gel capsule that encapsulates an edible oil.

* * * * *